(12) United States Patent
Jiang et al.

(10) Patent No.: US 12,242,198 B2
(45) Date of Patent: Mar. 4, 2025

(54) PHOTORESIST STRIPPING COMPOSITION

(71) Applicant: Dow Global Technologies LLC, Midland, MI (US)

(72) Inventors: Xin Jiang, Shanghai (CN); Stephen W. King, Braselton, GA (US)

(73) Assignee: Dow Global Technologies LLC, Midland, MI (US)

( * ) Notice: Subject to any disclaimer, the term of this patent is extended or adjusted under 35 U.S.C. 154(b) by 437 days.

(21) Appl. No.: 17/634,071

(22) PCT Filed: Aug. 30, 2019

(86) PCT No.: PCT/CN2019/103614
§ 371 (c)(1),
(2) Date: Feb. 9, 2022

(87) PCT Pub. No.: WO2021/035673
PCT Pub. Date: Mar. 4, 2021

(65) Prior Publication Data
US 2022/0365440 A1  Nov. 17, 2022

(51) Int. Cl.
| | |
|---|---|
| C11D 3/26 | (2006.01) |
| B08B 3/04 | (2006.01) |
| C07C 217/08 | (2006.01) |
| C11D 3/30 | (2006.01) |
| C11D 7/32 | (2006.01) |
| G03F 7/42 | (2006.01) |

(52) U.S. Cl.
CPC ............ *G03F 7/425* (2013.01); *C07C 217/08* (2013.01)

(58) Field of Classification Search
CPC ........... C11D 3/2006; C11D 3/26; C11D 3/30; C11D 7/32; B08B 3/04; G03F 7/42; G03F 7/425; C07C 217/08
See application file for complete search history.

(56) References Cited

U.S. PATENT DOCUMENTS

| | | | |
|---|---|---|---|
| 6,291,410 B1 | 9/2001 | Lallier | |
| 7,049,275 B2 | 5/2006 | Ikemoto et al. | |
| 9,574,126 B2 * | 2/2017 | Gamble | C09K 8/22 |
| 10,656,519 B2 | 5/2020 | Mukai | |

(Continued)

FOREIGN PATENT DOCUMENTS

| | | |
|---|---|---|
| CN | 101373343 B | 5/2012 |
| CN | 104216242 A | 12/2014 |

(Continued)

OTHER PUBLICATIONS

Office Action from corresponding Japanese Application: 2022-513428 with a mailing date of May 10, 2023.

(Continued)

*Primary Examiner* — Brian P Mruk

(57) ABSTRACT

A photoresist stripping composition comprising an organic amine and a method is provided. The photoresist stripping composition comprising an organic amine having the following formula (1).

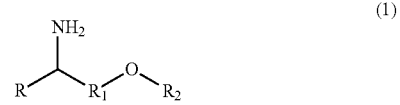

(1)

6 Claims, 2 Drawing Sheets

(56) References Cited

U.S. PATENT DOCUMENTS

| | | | | |
|---|---|---|---|---|
| 2015/0166867 A1* | 6/2015 | Gamble | .................. | C09K 8/22 |
| | | | | 507/133 |
| 2018/0066209 A1* | 3/2018 | Prasad | ................ | C11D 17/042 |
| 2019/0233771 A1 | 8/2019 | Mizutani et al. | | |

FOREIGN PATENT DOCUMENTS

| | | |
|---|---|---|
| CN | 106959589 A | 7/2017 |
| CN | 107357142 A | 11/2017 |
| CN | 107390482 A | 11/2017 |
| WO | 2014004193 A1 | 1/2014 |
| WO | 2018058341 A1 | 4/2018 |

OTHER PUBLICATIONS

PCT/CN2019/103614, International Search Report and Written Opinion with a mailing date of May 28, 2020.

\* cited by examiner

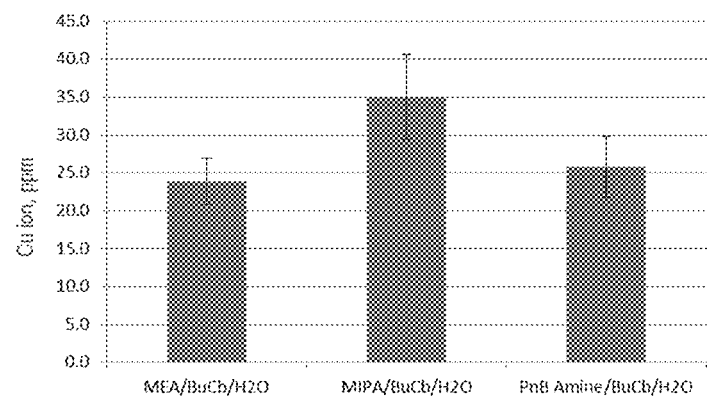
Figure 3
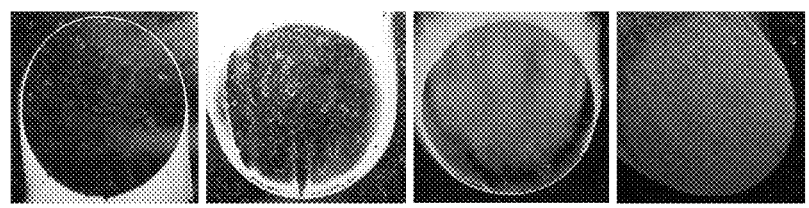
Figure 4a  Figure 4b  Figure 4c  Figure 4d
Figure 4

PHOTORESIST STRIPPING COMPOSITION

FIELD OF THE INVENTION

The present disclosure relates to a photoresist stripping composition, in particular a photoresist stripping composition for electronic manufacturing applications.

INTRODUCTION

Organic amines are widely used in a photoresist stripping and cleaning composition for electronics processing, such as a photoresist stripping composition for preparing RGB dyes in display, a photoresist stripping composition for a lithography process in semiconductor manufacturing, a photoresist stripping composition to remove a photoresist, a damaged photoresist layer, and a side-wall-protecting deposition film, etc., after dry or wet etching of wiring materials and electrode materials in the fabrication of semiconductor and display panel. The organic amines can dissolve many polar polymers, monomers, and compounds. However, the strong basic property of organic amines can cause the corrosion of metals such as copper and aluminum, thereby causing defects of the device such as wire board, semiconductor microchip and display pixel processed by a photoresist stripping and cleaning composition comprising an organic amine.

A conventional process for stripping or cleaning a photoresist is to dip a substrate with a photoresist into a photoresist stripping and cleaning composition. In recent years a spray stripping process is used for both semiconductor and display, in order to enhance the production efficacy, decrease the amount of the photoresist stripping and cleaning composition usage, and facilitate the treatment of large devices such as a large semi-conductor wafer and a large-screen display. During the spray stripping process, the stripping composition is sprayed on the substrate. However, a conventional photoresist stripping composition cannot be applied into this spraying stripping process, because the photoresist cannot be removed completely.

There is a need to provide a photoresist stripping and cleaning composition with weaker metal corrosion but good dissolution to electronic materials such as a photoresist.

SUMMARY OF THE INVENTION

The inventor has unexpectedly found that a photoresist stripping composition comprising a specific organic amine can have weaker metal corrosion but good dissolution to electronic materials such as a photoresist.

The present disclosure provides a photoresist stripping composition comprising an organic amine having the following formula (1):

(1)

wherein
R is hydrogen or an alkyl group having 1 to 12 carbons, $R_1$ is an alkylene group having 1 to 12 carbons, and $R_2$ is an alkyl group having 1 to 12 carbons.

The present disclosure further provides a method of stripping a photoresist, comprising:

(1) providing a substrate having a photoresist;
(2) spraying a photoresist stripping composition to the substrate or dipping the substrate into a photoresist stripping composition, wherein the photoresist stripping composition comprises an organic amine having the following formula (1):

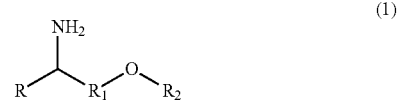

(1)

wherein
R is hydrogen or an alkyl group having 1 to 12 carbons, $R_1$ is an alkylene group having 1 to 12 carbons, and $R_2$ is an alkyl group having 1 to 12 carbons.

The present disclosure further provides use of an organic amine in a photoresist stripping composition, wherein said organic amine has the following formula (1):

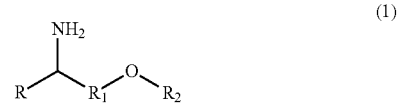

(1)

wherein
R is hydrogen or an alkyl group having 1 to 12 carbons, $R_1$ is an alkylene group having 1 to 12 carbons, and $R_2$ is an alkyl group having 1 to 12 carbons.

DESCRIPTION OF DRAWINGS

FIG. 3 shows copper ion contents measured in example 3.
FIG. 4 shows 4a-4d are photographs showing different stripping performances, obtained by Sony DSC-RX100M2.

DETAILED DESCRIPTION OF THE INVENTION

Figure 1:
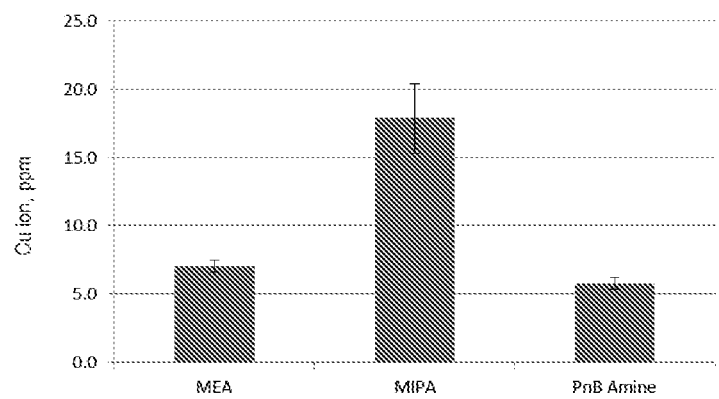
FIG. 1 shows copper ion contents measured in example 1.

As disclosed herein, the term "composition", "formulation" or "mixture" refers to a physical blend of different components, which is obtained by mixing simply different components by a physical means.

As disclosed herein, the term "stripping" or "cleaning" or "removing" have the same meaning, i.e., a photoresist is removed from a substrate.

As disclosed herein, all the percentages and parts of all components of the composition refer to the weight. All the percentages of all components of the composition are calculated based on the total weight of the composition. The sum of the percentages of all the components of the composition is 100%.

As disclosure herein, the term "alkyl" refers to a linear or branched alkyl group having 1 to 12 carbon atoms, typical 1 to 10 carbon atoms, more typical 1 to 6 carbon atoms, most typical 1 to 4 carbon atoms.

As disclosure herein, the term "alkylene" refers to a linear or branched alkylene group having 1 to 12 carbon atoms, typical 1 to 10 carbon atoms, more typical 1 to 6 carbon atoms, most typical 1 to 4 carbon atoms.

On one aspect, the present disclosure provides a photoresist stripping composition comprising an organic amine having the following formula (1):

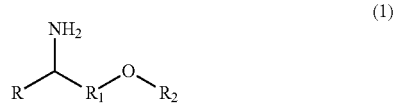

wherein
R is hydrogen or an alkyl group having 1 to 12 carbons, $R_1$ is an alkylene group having 1 to 12 carbons, and $R_2$ is an alkyl group having 1 to 12 carbons.

In one embodiment, R is an alkyl having 1 to 10 carbons, typical 1 to 8 carbons, more typical 1 to 6 carbons, most typical 1 to 4 carbons. In particular, R is hydrogen, methyl, ethyl, propyl, isopropyl, isobutyl or butyl.

In one embodiment, R is an alkylene having 1 to 10 carbons, typical 1 to 8 carbons, more typical 1 to 6 carbons, most typical 1 to 4 carbons. In particular, R is methylene, ethylene, propylene or butylene.

In one embodiment, R is an alkyl having 1 to 10 carbons, typical 1 to 8 carbons, more typical 1 to 6 carbons, most typical 1 to 4 carbons. In particular, R is methyl, ethyl, propyl, isopropyl, isobutyl or butyl.

In embodiment, the organic amine having the above formula (1) comprises, but not limited to, the following compounds: 1-butoxy-2-aminopropane, 1-methoxy-2-aminopropane, 1-ethoxy-2-aminopropane, 1-propoxy-2-aminopropane, 1-isobutoxy-2-aminopropane, 1-n-amyloxy-2-aminopropane, 1-butoxy-2-aminobutane, 1-methoxy-2-aminobutane, 1-ethoxy-2-aminobutane, 1-propoxy-2-aminobutane, or 1-isobutoxy-2-aminobutane.

Without wishing to be limited by theory, it is believed that the higher alkalinity of the organic amine of formula (1) improves the ability of the photoresist to penetrate and decompose the polymer chain in the photoresist, thus improving the photoresist stripper.

Generally, the photoresist stripping composition comprises 0.1-100 wt % of said organic amine, typical 1-70 wt %, more typical 5-60 wt %, most typical 10-50 wt %, based on the total weight of the photoresist stripping composition.

The composition may further comprise a solvent. The solvent solubilizes ionic components both in the photoresist and in the photoresist residues. Suitable solvents include, but are not limited to, glycol solvents such as ethylene glycol and propylene glycol, glycol ethers, alcohols, amides, carbonates, as well as combinations comprising at least one of the foregoing solvents.

Examples of the glycol ethers may include ethylene glycol methyl ether, ethylene glycol ethyl ether, ethylene glycol propyl ether, ethylene glycol butyl ether, diethylene glycol methyl ether, diethylene glycol ethyl ether, diethylene glycol butyl ether, diethylene glycol propyl ether, triethylene glycol methyl ether, triethylene glycol ethyl ether, triethylene glycol propyl ether, triethylene glycol butyl ether, propylene glycol methyl ether, propylene glycol ethyl ether, propylene glycol propyl ether, propylene glycol butyl ether, dipropylene glycol methyl ether, dipropylene glycol ethyl ether, dipropylene glycol butyl ether, dipropylene glycol propyl ether, tripropylene glycol methyl ether, tripropylene glycol ethyl ether, tripropylene glycol butyl ether, etc.

In an exemplary embodiment, the composition of the present disclosure comprises 0-90 wt % of a solvent, typical 10-80 wt %, more typical 20-75 wt %, most typical 30-70 wt %, based on the total weight of the composition.

The composition may further comprise water. In an exemplary embodiment, the composition of the present disclosure comprises 0-50 wt % of water, typical 0-40 wt %, more typical 0-35 wt %, most typical 0-30 wt %, based on the total weight of the composition.

The composition of the present disclosure may further comprise a corrosion inhibitor. The corrosion inhibitor may include a compound containing a nitrogen atom, a sulfur atom, an oxygen atom, etc., which have an unshared electron pair. Particularly, the compound may contain a hydroxyl group, a hydrogen sulfide group, etc. A reacting group of the corrosion inhibitor may physically and chemically adhere to a metal to prevent a corrosion of a metal thin layer including the metal.

The corrosion inhibitor includes a triazole compound. Examples of the triazole compound may include benzotriazole, tolyltrizole, etc.

The composition of the present disclosure may include 0-10 wt %, typical 0.1-8 wt %, more typical 0.5-5 wt %, most typical 1-3 wt % of the corrosion inhibitor, based on the total weight of the composition.

The composition of the present disclosure may further comprise a surfactant. The surfactant may be added in order to assist in both the lifting-off of insoluble photoresist residues and reduce silicon etching, which may occur under exposure to strong bases. Suitable surfactants include, but are not limited to, anionic, cationic, nonionic surfactants, such as fluoroalkyl surfactants, polyethylene glycols, polypropylene glycols, polyethylene or polypropylene glycol ethers, carboxylic acid salts, dodecylbenzenesulfonic acid or salts thereof, polyacrylate polymers, silicone or modified silicone polymers, acetylenic diols or modified acetylenic diols, alkylammonium or modified alkylammonium salts, as well as combinations comprising at least one of the foregoing surfactants.

In an exemplary embodiment, the composition of the present invention comprises 20 wt % or less of the surfactant, typical 15 wt % or less, more typical 1-10 wt %, based on the total weight of the composition.

The composition of the present disclosure may further comprise an alkanolamine compound. The alkanolamine compound suitable for use in the present disclosure can be represented by the chemical formula:

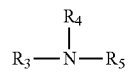

wherein $R_3$ and $R_4$ can be H, alkyl, aryl, alkylaryl, arylalkyl, alkyl alcohol, aryl alcohol, alkyaryl alcohol or arylalkyl alcohol and $R_5$ is alkyl alcohol, aryl alcohol, alkyaryl alcohol or arylalkyl alcohol or the like.

Examples of suitable alkanolamines include diethylene glycolamine (DGA), monoethanolamine, 2-(N-methylamino) ethanol, diethanolamine, triethanolamine, tertiary-butyldiethanolamine isopropanolamine, diisopropanolamine, 2-amino-1-propanol, 3-amino-1-propanol, isobutanolamine, 2-amino-2-ethoxyethanol, and 2-amino-2-ethoxy-propanol, 2-(2-hydroxylethylamino)ethanol, 2-(N-hydroxyethyl-amino)-ethanol, 1-hydroxy-2-aminobenzene, 2-[(2-aminoethyl)-(2-hydroxyethyl)-amino]-ethanol, 2-(2-aminoethoxy)ethanol, 2-(2-aminoethoxy)-propanol, N,N,N-tries(2-hydroxyethyl)-ammonia, N-aminoethyl-N'-hydroxyethyl-ethylenediamine, N,N'-dihydroxyethylethylenediamine, 2-[2-(2-aminoethoxy)-ethylamino]-ethanol, 2-[2-(2-aminoethylamino)-ethoxy]-ethanol, 2-[2-(2-aminoethoxy)-ethoxy]-ethanol, isopropanolamine, 3-amino-1-propanol, 2-amino-1-propanol, 2-(N-methylamino)ethanol, 2-(2-aminoethylamino)ethanol, tries (hydroxymethyl)aminoethane, triethanolamine, trimethanolamine, triisopropanolamine or mixtures thereof.

Generally, the photoresist stripping composition comprises 0.1-100 wt % of said organic amine and said alkanolamines, typical 1-70 wt %, more typical 5-60 wt %, most typical 10-50 wt %, based on the total weight of the photoresist stripping composition.

On another aspect, the present disclosure further provides a method of stripping a photoresist, comprising:

(1) providing a substrate having a photoresist;

(2) spraying a photoresist stripping composition to the substrate or dipping the substrate into a photoresist stripping composition, wherein the photoresist stripping composition comprises an organic amine having the following formula (1):

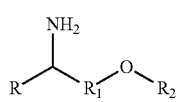

(1)

wherein

R is hydrogen or an alkyl group having 1 to 12 carbons, $R_1$ is an alkylene group having 1 to 12 carbons, and $R_2$ is an alkyl group having 1 to 12 carbons.

The photoresist as used herein is generally applicable to any layer comprising photoresist. Thus, for example, in accordance with the teachings of the present disclosure, the composition and method herein may be used to remove photoresist as well as photoresist residue.

The substrate as used herein includes, but not limited to, a semiconductor wafer, a printed wire board, an OLED display and a liquid crystal display. Generally, the substrate may further comprise a metal interconnect, such as copper interconnect, molybdenum interconnect and aluminum interconnect.

In an embodiment, the method may further comprise a step of rinsing the substrate obtained in step (2) with water.

On another aspect, the present disclosure further provides use of an organic amine in a photoresist stripping composition, wherein said organic amine has the following formula (1):

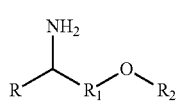

(1)

wherein

R is hydrogen or an alkyl group having 1 to 12 carbons, $R_1$ is an alkylene group having 1 to 12 carbons, and $R_2$ is an alkyl group having 1 to 12 carbons.

The organic amine according to the present disclosure may inhibit the corrosion of interconnect metal such as copper, molybdenum and aluminum.

EXAMPLES

Materials:

| Ingredient | Description | Source | Purity % |
|---|---|---|---|
| MEA | Monoethanolamine | Dow | 99 |
| MIPA | Monoisopropanolamine | Dow | 99 |
| PnB Amine | 1-butoxy-2-aminopropane | Dow | 99 |
| Butyl Carbitol | Diethylene glycol monobutyl ether | Dow | 99 |
| Deionized Water | $H_2O$ | Dow | Distilled |
| Photoresist | AZ SFP-1400 | AZ Electronic Materials | 70% photoresist, 30% PMA |
| Commercial stripper | Solvent-based stripper formulation | LG | 99 |
| Copper Foil III | Copper, 0.1 mm thick, plating | Dow | 99.99 |

Copper Corrosion Test

Copper Foil III was cut into 1 cm*1 cm pieces. The copper pieces were then immersed in a 2% HCl aqueous solution for 5 minutes in order to completely remove CuO or $Cu_2O$. Each copper piece was put in a 10 mL glass bottle with 5 g photoresist stripping formulation. The bottles were quickly shaked for two or three minutes and then were kept in an oven at 60° C. for 4 hours. Then, the copper pieces were taken out. ICP-OES (Perkin Elmer Optima 5300DV) was used to determine the content of copper ions remaining in the solvent.

Stripping Performance Test 2 mL of SFP-1400 photoresist solution was coated onto the surface of ITO glass substrate with the size of 100 mm×100 mm×1 mm. The substrate was spun at the rotation speed of 500 rpm for 10 seconds, and then the rotation speed was accelerated to 1000 rpm and maintained for 30 seconds. The spin-coated substrate was baked at 130° C. for 10 min to evaporate the solvent completely and cure the photoresist film. In the following stripping step, 0.5 ml stripping formulation was prepared in a container. The baked substrate was put into the container at 22° C., with shaking. The treated substrate was then washed by DI water for 15 seconds and dried on air. Then, the substrate was photographed by Sony DSC-RX100M2. According to FIG. 4a-4d, the stripping performance was ranked from 0 to 3:

3: excellent stripping performance, no PR residue (FIG. 4a)

2: good stripping performance, a little PR residue (FIG. 4b)

1: some PR residue (FIG. 4c)

0: can't remove PR at all (FIG. 4d)

Example 1

Pure Amine Used as a Stripping Formulation

MEA, MIPA (comparative examples), and PnB amine were used as a photoresist stripping formulation for copper corrosion test, respectively. The results were listed in FIG. 1.

MEA and MIPA showed higher Cu ion content than PnB amine after tests.

Example 2

Amine Solution as a Stripping Formulation

Figure 2:
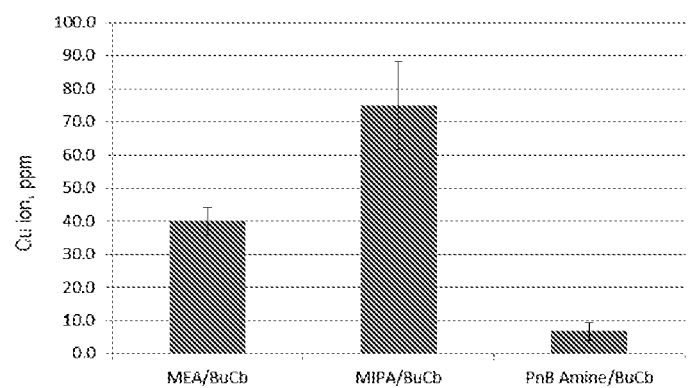
FIG. 2 shows copper ion contents measured in example 2.

Amines (MEA, MIPA or PnB amine) and Butyl Carbitol solvent were mixed with 3:7 ratios in order to study the Cu corrosion effect. The results were listed in FIG. 2.

MEA and MIPA showed much higher Cu ion content than PnB amine after tests, which means PnB amine with Butyl Carbitol showed superior corrosion effect to copper.

Example 3

Amine Solution as a Stripping Formulation

Amine (MEA, MIPA or PnB amine), Butyl Carbitol and water were mixed with 2.5:5:2.5 ratio in order to study the Cu corrosion effect. The results were listed in FIG. 3.

MIPA showed much higher Cu ion content than PnB amine and MEA after tests, which means PnB amine and MEA with Butyl Carbitol/water showed low corrosion effect to copper.

Example 4

The stripping performance of MEA, MIPA and PnB amine as single ingredient is evaluated.

| Ingredient | MEA | MIPA | PnB Amine | Commercial Stripper |
|---|---|---|---|---|
| Score | 3 | 3 | 3 | 3 |

PnB amine showed good stripping performance as MEA and MIPA.

Example 5

The stripping performance of solvent-based stripping formulations containing MEA, MIPA and AEEA was evaluated. Amine (MEA, MIPA or PnB amine): BuCb (Butyl Carbitol) weight ratio=3:7.

| Ingredient | MEA/BuCb | MIPA/BuCb | PnB Amine/BuCb | Commercial Stripper |
|---|---|---|---|---|
| Score | 3 | 3 | 3 | 3 |

The stripper containing PnB amine showed the same stripping capability with MEA/MIPA formulations and commercial stripper.

Example 6

The stripping performance of semi-aqueous stripper formulations containing MEA, MIPA and PnB amine was evaluated. Amine:BuCb:Water weight ratio=2.5:5:2.5.

| Ingredient | MEA/BuCb/H$_2$O | MIPA/BuCb/H$_2$O | PnB Amine/BuCb/H$_2$O | Commercial Stripper |
|---|---|---|---|---|
| Score | 3 | 3 | 3 | 3 |

The stripper containing PnB amine showed the same stripping capability with MEA/MIPA formulations and commercial stripper.

What is claimed is:

1. A method of stripping a photoresist, comprising:
   (1) providing a substrate having a photoresist wherein the substrate is selected from the group consisting of a semiconductor wafer, a printed wire board, an OLED display and a liquid crystal display;
   (2) spraying a photoresist stripping composition onto the substrate or dipping the substrate into a photoresist stripping composition, wherein the photoresist stripping composition comprises an organic amine having the following formula (1):

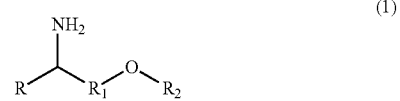

wherein
R is hydrogen or an alkyl group having 1 to 12 carbons, R$_1$ is an alkylene group having 1 to 12 carbons, and R$_2$ is an alkyl group having 1 to 12 carbons.

2. The method of claim 1, wherein R is an alkyl having 1 to 10 carbons, and wherein R$_1$ is an alkylene having 1 to 10 carbons.

3. The method of claim 1, wherein R$_1$ is an alkylene having 1 to 10 carbons.

4. The method of claim 1, wherein R$_2$ is an alkyl having 1 to 10 carbons.

5. The method of claim 1, wherein the organic amine having the above formula (1) comprises a material selected from the group consisting of: 1-butoxy-2-aminopropane, 1-methoxy-2-aminopropane, 1-ethoxy-2-aminopropane, 1-propoxy-2-aminopropane, 1-isobutoxy-2-aminopropane, 1-n-amyloxy-2-aminopropane, 1-butoxy-2-aminobutane, 1-methoxy-2-aminobutane, 1-ethoxy-2-aminobutane, 1-propoxy-2-aminobutane, and 1-isobutoxy-2-aminobutane.

6. The method of claim 1, wherein the photoresist stripping composition further comprises a polar solvent selected from the group consisting of water, glycol solvents, glycol ethers, alcohols, amides, carbonates, and combinations thereof.

* * * * *